United States Patent
Miklos et al.

(10) Patent No.: US 8,289,517 B2
(45) Date of Patent: Oct. 16, 2012

(54) METHOD AND DEVICE FOR MEASURING A PHOTOACOUSTIC SIGNAL WITH COMPUTER-ASSISTED EVALUATION

(75) Inventors: Andras Miklos, Stuttgart (DE); Judit Angster, Stuttgart (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 74 days.

(21) Appl. No.: 12/593,172

(22) PCT Filed: Mar. 27, 2008

(86) PCT No.: PCT/EP2008/002437
§ 371 (c)(1),
(2), (4) Date: Sep. 25, 2009

(87) PCT Pub. No.: WO2008/116657
PCT Pub. Date: Oct. 2, 2008

(65) Prior Publication Data
US 2010/0045991 A1    Feb. 25, 2010

(30) Foreign Application Priority Data
Mar. 27, 2007 (DE) .......... 10 2007 014 516

(51) Int. Cl.
*G01N 21/00* (2006.01)
(52) U.S. Cl. .......... 356/432; 356/433
(58) Field of Classification Search .......... 356/432–444; 250/343–345, 350–351, 339.09, 339.06, 250/565; 73/24.02, 592, 584, 25.01, 24.03
See application file for complete search history.

(56) References Cited

U.S. PATENT DOCUMENTS

| | | | |
|---|---|---|---|
| 4,200,399 | A | 4/1980 | Kimble et al. |
| 5,129,255 | A | 7/1992 | Corbin |
| 5,933,245 | A | 8/1999 | Wood et al. |
| 6,608,683 | B1 | 8/2003 | Pilgrim et al. |
| 7,710,566 | B2 * | 5/2010 | Arnott et al. .......... 356/432 |
| 2004/0179200 | A1 | 9/2004 | Yoon et al. |
| 2006/0123884 | A1 * | 6/2006 | Selker et al. .......... 73/24.02 |

FOREIGN PATENT DOCUMENTS
DE    199 25 196    12/2000
(Continued)

OTHER PUBLICATIONS

Slezak Veronica "Signal processing in pulsed photoacoustic detection of traces by means of a fast fourier transform-based method", vol. 74, No. 1, Jan. 1, 2003, pp. 642-644, XP012040332, ISSN: 0034-6748.

(Continued)

*Primary Examiner* — Tri T Ton
(74) *Attorney, Agent, or Firm* — Greenblum & Bernstein, P.L.C.

(57) ABSTRACT

A method for measuring a photoacoustic signal using light sources that emit light at different wavelengths, wherein the method comprises electing a scanning frequency with which signals are recorded, determining a modulation frequency for each light source by dividing the scanning frequency by an integer division value that is different for each light source, exciting a photoacoustic signal in a photoacoustic measuring cell using the light sources and the modulation frequency, measuring, with a sound pressure sensor, a produced sound pressure, digitizing a signal of the sound pressure sensor, determining a signal component assignable to a respective light source by evaluating a sequence of digitized measured values, and filtering out measured value components that occur periodically with a period of a respective modulation frequency.

19 Claims, 1 Drawing Sheet

FOREIGN PATENT DOCUMENTS

| | | |
|---|---|---|
| EP | 0 282 234 | 9/1988 |
| EP | 0 590 813 | 4/1994 |
| EP | 1 715 324 | 10/2006 |

OTHER PUBLICATIONS

Bellaiche-Sharpe P et al. "Real-Time Photoacoustic Signal Analysis in a Gas-Phase Spectrophone: A Feasibility Study" vol. 50, No. 11, Nov. 1, 1996, pp. 1366-1372, XP000642383, ISSN: 0003-7028, p. 1366, right-hand colum, lines 23-26; figure 1 pp. 1367-1369.

Beenen A et al. "Development of a Photoacoustic Trace Gas Sensor Based on Fiber-Optically Coupled NIR Laser Diodes", vol. 53, No. 9, Sep. 1, 1999, pp. 1040-1044, XP000903098, ISSN: 0003-7028 figure 1.

C. Brand et al. "Pulsed-laser excitation of acoustic modes in open high-Q photoacoustic resonators for trace gas monitoring: results for C2H4" vol. 34, No. 18, Jun. 20, 1995, pp. 3257-3266, XP002486473 table 1.

* cited by examiner

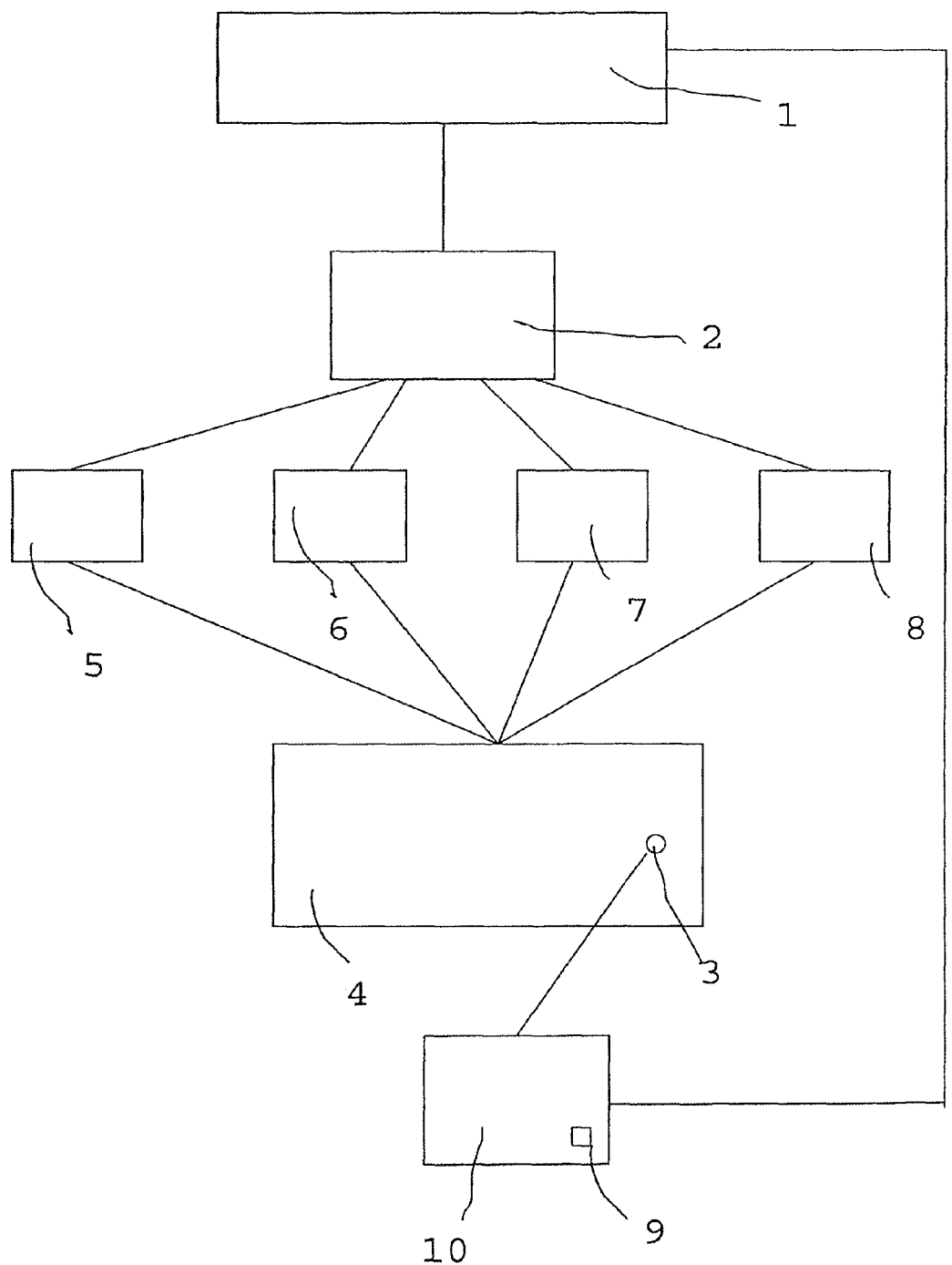

METHOD AND DEVICE FOR MEASURING A PHOTOACOUSTIC SIGNAL WITH COMPUTER-ASSISTED EVALUATION

CROSS-REFERENCE TO RELATED APPLICATIONS

The present application is a U.S. National Stage of International Patent Application No. PCT/EP2008/002437 filed Mar. 27, 2008 which published as WO 2008/116657 on Oct. 2, 2008, and claims priority of German Patent Application No. 10 2007 014 516.2 filed Mar. 27, 2007.

BACKGROUND OF THE INVENTION

1. Field of the Invention

The invention relates to method for measuring the photoacoustic signal with computer-assisted evaluation.

2. Discussion of Background Information

Photoacoustic spectroscopy is becoming increasingly used as a measuring method to determine the presence or concentration of substances that absorb light. Excitation by means of light is used that is absorbed by the substances to be investigated. The absorption generates heat which causes the surrounding gas, liquid or solid body to expand. A pressure wave is generated by this heat. When periodic or pulsed excitation is used, it can generate a sound wave. This sound wave can be measured by means of a sound pressure sensor. The signal obtained thereby is a measure of the concentration of the substances to be investigated. A widespread measurement option is excitation by means of a modulated light source. When the excitation light is modulated, the corresponding acoustic signal must also be modulated. This insight is used to suppress the background signal. It is conventional to use lock-in amplifiers which use complicated electronics to filter out of the obtained signal those components that correspond to the modulation frequency. In this manner it is also possible to investigate several substances one after the other using different light sources that emit light at different wavelengths and are modulated with the modulation frequency. It is also possible to measure two substances simultaneously using two light sources that are modulated with the same modulation frequency but are modulated in antiphase. The disadvantage here is that the required measuring technique is very complicated and hence very expensive.

A set-up is for example known from U.S. Pat. No. 6,608,683 B1 in which a modulation frequency is provided by means of which the optical radiation entering the resonant photoacoustic measuring cell is modulated. The modulation frequency is simultaneously transmitted to a lock-in amplifier. The signal originating from a microphone is also transmitted to the lock-in amplifier. There, those signal components that correspond to the modulation frequency are amplified. The modulation frequency is adjusted depending on the determined photoacoustic signal.

U.S. Pat. No. 5,129,255 discloses a complex electronic circuit with which the signal obtained is amplified by resonant excitation of a photoacoustic measuring cell.

A photoacoustic measuring arrangement is known from EP 1 715 324 A1 for detecting gases and/or aerosols. This arrangement has a measuring cell and reference cell. The difference signal from the microphone of the measuring cell and the microphone of the reference cell is transmitted to a difference amplifier from where it is sent to a phase-sensitive rectifier, i.e. a lock-in amplifier.

A photoacoustic measuring arrangement is known from U.S. Pat. No. 4,200,399 in which the radiation originating from a radiation source is modulated by means of a known reference frequency. The modulated radiation is used to excite sound waves in a measuring cell by means of absorption, which sound waves are detected by a microphone. The microphone signal is transmitted to a lock-in amplifier. In the lock-in amplifier, those signals are amplified that correspond to a reference frequency.

SUMMARY OF THE INVENTION

The invention aims to overcome the disadvantages of the prior art and to provide an economical method and associated device by way of which several substances to be investigated can be measured simultaneously.

The invention also provides for a method for measuring a photoacoustic signal using light sources that emit light at different wavelengths, wherein the method comprises electing a scanning frequency with which signals are recorded, determining a modulation frequency for each light source by dividing the scanning frequency by an integer division value that is different for each light source, exciting a photoacoustic signal in a photoacoustic measuring cell using the light sources and the modulation frequency, measuring, with a sound pressure sensor, a produced sound pressure, digitizing a signal of the sound pressure sensor, determining a signal component assignable to a respective light source by evaluating a sequence of digitized measured values, and filtering out measured value components that occur periodically with a period of a respective modulation frequency.

The filtering out may occur via a calculation method and the exciting comprises simultaneously exciting a photoacoustic signal in a photoacoustic measuring cell using the light sources and the modulation frequency. A number of the sequence of digitized measured values may correspond to a product of a selected multiplication value and a respective division value. A number of the sequence of digitized measured values may correspond to a product of a multiplication value and a respective division value. The multiplication value may be one of an even number and a power of 2.

The method may further comprise dividing the sequence of digitized measured values into two partial sequences of equal length, adding values of the two partial sequences such that an nth value of a first partial sequence is added to an nth value of a second partial sequence, and calculating a root-mean-square value.

The method may further comprise dividing the sequence of digitized measured values into two partial sequences of equal length, adding values of the two partial sequences such that an nth value of a first partial sequence is added to an nth value of a second partial sequence, and carrying out the adding a maximum of m times, wherein the multiplication value is $2^m$ and "m" is a positive integer.

The method may further comprise calculating a mean value using a Fourier sequence.

The method may further comprise amplifying the photoacoustic signal via resonance in the photoacoustic measuring cell.

The method may further comprise utilizing a division value of approximately 50.

The method may further comprise modulating each light source such that an initial intensity is a sum of a constant and one of a rectangle function and a sinusoidal function.

The method may further comprise modulating wavelengths of the light sources.

The invention also provides for a device configured to implement the method described above, wherein the device comprises a quartz oscillator structured and arranged to provide a scanning frequency, a counter structured and arranged to provide modulation frequencies that result from dividing the scanning frequency by an integer division value, light sources structured and arranged to provide excitation light at different wavelengths at respective modulation frequencies, at least one sound pressure sensor configured to measure a sound pressure, an analog-digital converter configured to digitize a measured signal, and a computer configured to save a digitized measured values and perform a calculation that filters out measured value components that are periodic with a period of a modulation frequency.

The invention also provides for a photoacoustic measuring system for determining several contaminants that absorb at different wavelengths emitted from respective light sources, wherein the system comprises the device described above.

The invention also provides for a device for measuring a photoacoustic signal using light sources that emit light at different wavelengths, wherein the device comprises a quartz oscillator structured and arranged to provide a scanning frequency, a counter structured and arranged to provide modulation frequencies that result from dividing the scanning frequency by an integer division value, light sources structured and arranged to provide excitation light at different wavelengths at respective modulation frequencies, at least one sound pressure sensor configured to measure a sound pressure, an analog-digital converter configured to digitize a measured signal, and a computer configured to save a digitized measured values and perform a calculation that filters out measured value components that are periodic with a period of a modulation frequency.

The invention also provides for a photoacoustic measuring system for determining several contaminants that absorb at different wavelengths emitted from respective light sources, wherein the system comprises a device comprising a quartz oscillator structured and arranged to provide a scanning frequency, a counter structured and arranged to provide modulation frequencies that result from dividing the scanning frequency by an integer division value, light sources structured and arranged to provide excitation light at different wavelengths at respective modulation frequencies, at least one sound pressure sensor configured to measure a sound pressure, an analog-digital converter configured to digitize a measured signal, and a computer configured to save a digitized measured values and perform a calculation that filters out measured value components that are periodic with a period of a modulation frequency. The device comprises the following modes of operation; selecting a scanning frequency with which signals are recorded, determining a modulation frequency for each light source by dividing the scanning frequency by an integer division value that is different for each light source, exciting a photoacoustic signal, measuring the sound pressure, digitizing a signal of the at least one sound pressure sensor, determining a signal component assignable to a respective light source by evaluating a sequence of digitized measured values, and filtering out measured value components that occur periodically with a period of a respective modulation frequency.

It was recognized that a method needs to be provided for measuring a photoacoustic signal in an excitation with several light sources that emit light at different wavelengths. This method is designed to avoid the use of a complicated measuring technique. This method comprises the following aspects discussed below.

A scanning frequency is selected by way of which the signal of the sound pressure sensor is to be digitized. The frequency is typically within the range of several hundred kilohertz. Furthermore, a modulation frequency is selected for each light source. The modulation frequency results from dividing the scanning frequency with a integer division value that is different for each light source. Whereas a certain amount of imprecision is tolerable for the modulation frequency, the division value should be maintained very exactly. However, this is reliably achieved, for example, with a counter that is suitable for providing modulation frequencies that result from dividing the scanning frequency. This results in a simultaneous excitation with the light sources that emit light at different wavelengths with the specified but different modulation frequencies. The sound pressure produced, i.e., the photoacoustic signal, is measured with a sound pressure sensor, normally a microphone. The obtained measurement signal is digitized with the scanning frequency. The signal components to be assigned to the respective light source are determined by evaluating a sequence of digitized measured values. The number of measured values in the sequence results from the product of a selected multiplication value (as disclosed later, this is the number of the selected periods) with the above-cited division value. This ensures that a sequence of the same number of complete periods of the respective modulation is available for evaluation. The number of periods corresponds to the selected multiplication value. This will be illustrated by way of the following calculations. It should first be noted that the duration of a modulation period corresponds to the inverse value of the modulation frequency. The number of measured values within a modulation period is the product of the scanning frequency and duration of a modulation period. Since the modulation frequency results from dividing the scanning frequency by the division value, the duration of a period, i.e., the inverse value of the modulation frequency, is accordingly the ratio of the division value to the scanning frequency. The number of measured values in a modulation period is therefore the product of the scanning frequency with the ratio of the division value to the scanning frequency. The number of measured values in a modulation is therefore equal to the division value. This will be again clarified below:

Duration of modulation period=1/modulation frequency (1)
Measured values per modulation period=duration of modulation period*scanning frequency (2)
Modulation frequency=scanning frequency/division value (3)
(3) in (1)
Duration of modulation periods=division value/scanning frequency (4)
(4) in (2)
Measured values per modulation period=division value/scanning frequency*scanning frequency
Measured values per modulation periods=division value (5)

In a surprisingly simple manner, it can thus be ensured that a sequence of entire modulation periods is selected for the respective light source. It is therefore comparatively easy to use a calculation method to filter out the measured value components that are periodic with the period of the modulation frequency.

For the sake of completeness, it is noted that the individual steps do not all have to be performed in the above-cited sequence.

It is noted that the different light sources can also be realized by spectrally dividing light originating from one light source. Of course, to perform the above-described method, it must be possible to modulate the spectrally divided light.

A particularly simple calculation method for evaluation requires the multiplication value to be an even number, especially a power of two, i.e., equal to $2^m$, where m is even and positive. A calculation with the following steps can then be used. The number of individual, digitized measured values in the selected sequence is the multiplication value multiplied by the division value. The sequence of the digitized measured values is divided into two partial sequences of equal length. The values of the partial sequences are added such that the nth value of the first partial sequence is added to the nth value of the second partial sequence. This ensures that the respectively appropriate values are added. Accordingly, values at the beginning of a period are added to values at the beginning of the corresponding period of the other partial sequence, values in the middle of a period are added to values in the middle of the corresponding period of the next partial sequence, and values at the end of the period are added to values at the end of the corresponding period in the next partial sequence. Only the periodically corresponding signals are thereby amplified. The random, i.e., aperiodic noise signal arising from electronic or mechanical disturbances in the sound pressure sensor and the evaluation electronics as well as general background noise is thereby not amplified, in fact is even equalized. In particular, the signals that arise from excitation with different modulation frequencies are not amplified. This is also related to the type of sound pressure, which can be positive or negative since these are sound waves. If the sound pressure sensor has a membrane, a high sound level is not shown in that the membrane is deflected in one direction from a rest position and remains there. Instead, the membrane oscillates around the rest position driven by the sound waves. The described process steps of halving the sequences and adding the thereby obtained partial sequences can be repeated until only one period remains that contains a number of measurement data corresponding to the division value. If the division value equals $2^m$, these process steps can be performed m times until precisely one whole period remains. The more the method is repeated, the more precise the measurement data.

One suitable option for further evaluation is to subsequently square the thereby obtained values, add the squares, and calculate the root of the sum of squares, i.e., to calculate the root-mean-square value. This calculation ensures that the contributions from negative sound pressure also appear as a positive signal. In addition, higher amplitudes contribute more to the signal. This additionally helps to suppress the noise signal.

Alternatively, instead of calculating the root of the sum of the squares, the average of the values can be calculated. The method most suitable for determining the concentration depends on the individual case and is ultimately to be determined by calibration. It is also possible to calculate the components of the Fourier series.

A higher multiplication value and hence the evaluation of a larger number of modulation periods generally has the advantage that distinguishing which excitation wavelength contributes to the signal to which degree is more precise. This becomes clear when we consider the almost completely unsuitable extreme case of 2 as the multiplication value. The above-described evaluation method is based on the fact that adding the nth value of a period to the corresponding nth value of the next period amplifies only the periodically occurring values. If the duration of the modulation periods and the modulation frequencies differs only slightly, in the second modulation period the signal that originates from an excitation with a modulation frequency that differs from that to be evaluated has approximately the same characteristic as in the first modulation period.

Particularly high sensitivity is achieved when the modulation frequencies are so close to the resonance frequency of the utilized measuring cell that the photoacoustic signal is amplified by resonance in the photoacoustic cell. It is clear that the modulation frequency can be exactly the same as the resonance frequency for at the most one excitation light source. The other modulation frequencies must differ slightly. However, when the scanning frequency and division value are sufficiently high, the differences in the modulation frequencies are acceptably low enough for the amplification to be sufficiently high for each modulation frequency.

To be able to carry out resonant measurements, a suitable value for the division value is approximately 50. Of course, only one division value can be exactly 50, and the others must be different integers. The maximum scanning frequency of an A/D converter obtainable at an acceptable price is generally not more than 500 kHz. The quality factor (Q factor) of the conventional resonators is approximately 20. By definition, the Q factor is the quotient of the resonant frequency and half-width. Since the resonance frequency is normally in the range of several thousand hertz, a division value of approximately 50 should be selected so that all the modulation frequencies can be close to the resonance frequencies.

A simple modulation of the light source is achieved by setting the initial intensity of the light source to be the sum of a constant and a rectangle function or sinusoidal function. If a diode laser is chosen as the light source, for example, it is sufficient to regulate the current accordingly.

To provide a device for implementing the above-cited method, a quartz oscillator is required that provides the corresponding scanning frequency. A counter is also necessary that is suitable for providing modulation frequencies obtained by dividing the scanning frequency by a integer division value. In addition, several light sources are necessary that can provide excitation light at different wavelengths at the respective modulation frequencies for excitation. In addition, a sound pressure sensor that can measure the sound pressure is required. Furthermore, an analog-digital converter is necessary that can digitize the measured signal. Finally, a computer is required that is designed to save the digitized measured values and that can perform a calculation that filters out the measured value components that are periodic with the period of the modulation frequency. Of course, the digitized measured values do not have to be saved in the computer itself; they can be saved in a data storage unit. All of these cited components are standard components that as mass produced goods are easily obtained at a low price. In particular, it is possible to replace the previously required lock-in amplifier with a computer that is generally available anyway and a simple analog-digital converter card. This significant reduction in expenditure in terms of equipment, makes it possible to also use the method and measuring device for applications in which photoacoustic measurement has previously not been considered due to the high expense.

With the above-described device, a photoacoustic measuring system can be realized in a particularly simple manner for determining several contaminants that absorb at different wavelengths emitted from the respective light sources.

BRIEF DESCRIPTION OF THE DRAWINGS

The invention is described in more detail below with reference to an exemplary embodiment without restricting the general application wherein:

The sole FIGURE shows a chart of a photoacoustic signal measuring system in accordance with the invention.

DETAILED DESCRIPTION OF THE INVENTION

FIG. 1 shows a schematic setup of the measuring arrangement. A quartz oscillator 1 provides a scanning frequency of $f_s$=320 kHz. This scanning frequency is transmitted to the counter 2 and to the analog/digital converter 9. The counter 2 divides the scanning frequency provided by the quartz oscillator 1 clearly into individual modulation frequencies. A division value of 50 is used to provide the first modulation frequency $f_{m1}$. The first modulation frequency is therefore $f_s/50$=6400 Hz. A division value of 49 is used to provide the second modulation frequency $f_{m2}$. The second modulation frequency $f_{m2}$ is therefore $f_s/49$=6530.6 Hz. The division value for the third modulation frequency $f_{m3}$ is 48, which yields the third modulation frequency of $f_s/48$=6666.7 Hz. The fourth modulation frequency $f_{m4}$ is finally yielded at $f_s/47$=6808.5 Hz since the division value 47 is selected. Because the photoacoustic cell 4 has a resonance frequency of 6600 Hz and a Q factor of 15, the modulation frequencies thus achieved are all close to the resonance frequency. With the Q factor 15, a half-width of the resonance curve of 6600/15=440 Hz results by definition. Even at a frequency of 6380 Hz on the one hand and 6820 Hz on the other, a resonance amplification can still be obtained that is approximately 0.7 times as large as the resonance amplification at 6600 hertz. The respective modulation frequencies are used to modulate assigned diode lasers. The current applied to the lasers 5, 6, 7, and 8 is thereby modulated to produce a square-wave current flow with the modulation frequency. The resulting radiation from the diode lasers is focused and introduced by means of optical waveguides into the photoacoustic cell 4 in which the substances to be investigated are located. The sound pressure sensor 3 measures the sound pressure in the photoacoustic cell 4. The thereby obtained sound signal is digitized in the analog-digital converter 9, which can be integrated in the computer 10 with the scanning frequency $f_s$ provided by the quartz oscillator 1. The measured values are transmitted to the computer 10. A sequence 256 kB long is thereby saved in the computer 10.

Then 4096 (=$2^{12}$) complete periods are selected for the individual modulation frequencies in each case. As explained above, the number of measured values in a period is equal to the division value. Accordingly, 4096*50=204,800 measured values are selected for the first division value of 50, 4096*49=200,704 measured values are selected for the division value of 49, 4096*48=196,608 measured values are selected for the third division value of 48, and finally 4096*47=192,512 measured values are selected for the fourth division value of 47. The data are then evaluated separately for each modulation frequency.

First the 204,800 measured values for the modulation frequency of 6400 Hz, i.e., a division value of 50, are evaluated. The 4096 periods are divided into two partial sequences of 2048 periods each. Then the two partial sequences are added. The addition is carried out such that in each case the first value of the first partial sequence is added to the first value of the second partial sequence, the second value of the first partial sequence is added to the second value of the second partial sequence, etc. until the last value of the first partial sequence is added to the last value of the second partial sequence. The new partial sequence with 2048 values obtained in this manner is then subjected to the above procedure. The measured values are thus halved again, then the sequence of 2048 values is divided into two partial sequences of 1024 values each, and then the addition is performed in the described manner. This procedure is performed a total of 12 times. Finally, a single period is obtained. This period contains as many measuring points as the division value. Now the individual measured values are squared. The obtained squares are added. Then the root is calculated from the sum of the squares. Finally, this is divided by the number of measured values, i.e., by the division value 50. The obtained value is a measure of the sound pressure that is to be assigned to the signal of the modulation frequency of 6400 Hz.

This method is then repeated for the other modulation frequencies. To avoid misunderstanding, it is stressed that essentially the same photoacoustic signal is to be evaluated in the evaluation of the different modulation frequencies. Only a different number of measured values of the digitized and saved sequence is evaluated. Let us assume that a total of 205,000 measured values are saved in the sequence. In this case, the first 204,800 measured values can be used to evaluate the first modulation frequency $f_{m1}$, the first 200,704 measured values can be used to evaluate the second modulation frequency $f_{m2}$, the first 196,608 measured values can be used to evaluate the third modulation frequency $f_{m3}$, and the first 192,512 measured values can be used to evaluate the fourth modulation frequency $f_{m4}$.

LIST OF REFERENCE NUMBERS

1 Quartz oscillator
2 Counter
3 Sound pressure sensor
4 Photoacoustic cell
5 1st diode laser
6 $2^{nd}$ diode laser
7 $3^{rd}$ diode laser
8 $4^{th}$ diode laser
9 Analog-digital converter
10 Computer

The invention claimed is:

1. A method for measuring a photoacoustic signal using light sources that emit light at different wavelengths, the method comprising:
   selecting a scanning frequency with which signals are recorded;
   determining a modulation frequency for each light source by dividing the scanning frequency by an integer division value, said integer division value being different for each light source;
   exciting a photoacoustic signal in a photoacoustic measuring cell by simultaneously providing excitation light at different wavelengths using the light sources and the modulation frequency;
   measuring, with a sound pressure sensor, a produced sound pressure;
   digitizing a signal of the sound pressure sensor;
   determining a signal component assignable to a respective light source by evaluating a sequence of digitized measured values; and
   filtering out measured value components that occur periodically with a period of a respective modulation frequency.

2. The method of claim 1, wherein the filtering out occurs via a calculation method and the exciting comprises simultaneously exciting a photoacoustic signal in a photoacoustic measuring cell using the light sources and the modulation frequency.

3. The method of claim 1, wherein a number of the sequence of digitized measured values corresponds to a product of a selected multiplication value and a respective division value.

4. The method of claim 1, wherein a number of the sequence of digitized measured values corresponds to a product of a multiplication value and a respective division value.

5. The method of claim 4, wherein the multiplication value is one of an even number and a power of 2.

6. A method for measuring a photoacoustic signal using light sources that emit light at different wavelengths, the method comprising:
- selecting a scanning frequency with which signals are recorded;
- determining a modulation frequency for each light source by dividing the scanning frequency by an integer division value that is different for each light source;
- exciting a photoacoustic signal in a photoacoustic measuring cell by simultaneously providing excitation light at different wavelengths using the light sources and the modulation frequency;
- measuring, with a sound pressure sensor, a produced sound pressure;
- digitizing a signal of the sound pressure sensor;
- determining a signal component assignable to a respective light source by evaluating a sequence of digitized measured values;
- filtering out measured value components that occur periodically with a period of a respective modulation frequency;
- dividing the sequence of digitized measured values into two partial sequences of equal length;
- adding values of the two partial sequences such that an nth value of a first partial sequence is added to an nth value of a second partial sequence; and
- calculating a root-mean-square value.

7. A method for measuring a photoacoustic final using light sources that emit light at different wavelengths, the method comprising:
- selecting a scanning frequency with which signals are recorded;
- determining a modulation frequency for each light source by dividing the scanning frequency by an integer division value that is different for each light source;
- exciting a photoacoustic signal in a photoacoustic measuring cell by simultaneously providing excitation light at different wavelengths using the light sources and the modulation frequency;
- measuring, with a sound pressure sensor, a produced sound pressure;
- digitizing a signal of the sound pressure sensor;
- determining a signal component assignable to a respective light source by evaluating a sequence of digitized measured values; and
- filtering out measured value components that occur periodically with a period of a respective modulation frequency,
- wherein a number of the sequence of digitized measured values corresponds to a product of a multiplication value and a respective division value,
- and further comprising:
- dividing the sequence of digitized measured values into two partial sequences of equal length;
- adding values of the two partial sequences such that an nth value of a first partial sequence is added to an nth value of a second partial sequence; and
- carrying out the adding a maximum of m times,
- wherein the multiplication value is $2^m$ and "m" is a positive integer.

8. The method of claim 1, further comprising:
calculating a mean value using a Fourier sequence.

9. The method of claim 1, further comprising:
amplifying the photoacoustic signal via resonance in the photoacoustic measuring cell.

10. The method of claim 1, further comprising:
utilising a division value of approximately 50.

11. A method for measuring a photoacoustic signal using light sources that emit light at different wavelengths, the method comprising:
- selecting a scanning frequency with which signals are recorded;
- determining a modulation frequency for each light source by dividing the scanning frequency by an integer division value that is different for each light source;
- exciting a photoacoustic signal in a photoacoustic measuring cell by simultaneously providing excitation light at different wavelengths using the light sources and the modulation frequency;
- measuring, with a sound pressure sensor, a produced sound pressure;
- digitizing a signal of the sound pressure sensor;
- determining a signal component assignable to a respective light source by evaluating a sequence of digitized measured values;
- filtering out measured value components that occur periodically with a period of a respective modulation frequency; and
- modulating each light source such that an initial intensity is a sum of a constant and one of a rectangle function and a sinusoidal function.

12. The method of claim 1, further comprising:
modulating wavelengths of the light sources.

13. A device configured to implement the method of claim 1, the device comprising:
- a quartz oscillator structured and arranged to provide a scanning frequency;
- a counter structured and arranged to provide modulation frequencies that result from dividing the scanning frequency by an integer division value;
- light sources structured and arranged to provide excitation light at different wavelengths at respective modulation frequencies;
- at least one sound pressure sensor configured to measure a sound pressure;
- an analog-digital converter configured to digitize a measured signal; and
- a computer configured to save a digitized measured values and perform a calculation that filters out measured value components that are periodic with a period of a modulation frequency.

14. A photoacoustic measuring system for determining several contaminants that absorb at different wavelengths emitted from respective light sources, the system comprising the device of claim 13.

15. A device for measuring a photoacoustic signal using light sources that emit light at different wavelengths, the device comprising:
- a quartz oscillator structured and arranged to provide a scanning frequency;
- a counter structured and arranged to provide modulation frequencies that result from dividing the scanning frequency by an integer division value, said integer divisional value being different for each light source;
- said light sources structured and arranged to simultaneously provide excitation light at different wavelengths at respective modulation frequencies;
- at least one sound pressure sensor configured to measure a sound pressure;
- an analog-digital converter configured to digitize a measured signal; and a computer configured to save a digitized measured values and perform a calculation that filters out measured value components that are periodic with a period of a modulation frequency.

16. A photoacoustic measuring system for determining several contaminants that absorb at different wavelengths emitted from respective light sources, the system comprising:
  a device comprising:
    a quartz oscillator structured and arranged to provide a scanning frequency;
    a counter structured and arranged to provide modulation frequencies that result from dividing the scanning frequency by an integer division value;
    light sources structured and arranged to simultaneously provide excitation light at different wavelengths at respective modulation frequencies;
    at least one sound pressure sensor configured to measure a sound pressure;
    an analog-digital converter configured to digitize a measured signal; and
    a computer configured to save a digitized measured values and perform a calculation that filters out measured value components that are periodic with a period of a modulation frequency; and
  the device comprising the following modes of operation:
    selecting a scanning frequency with which signals are recorded;
    determining a modulation frequency for each light source by dividing the scanning frequency by an integer division value, said integer division value being different for each light source;
    exciting a photoacoustic signal;
    measuring the sound pressure;
    digitizing a signal of the at least one sound pressure sensor;
    determining a signal component assignable to a respective light source by evaluating a sequence of digitized measured values; and
    filtering out measured value components that occur periodically with a period of a respective modulation frequency.

17. The system of claim 16, wherein the system is structured and arranged to determine several contaminants that absorb at different wavelengths emitted from the respective light sources.

18. The device of claim 15, wherein the device is structured and arranged to determine several contaminants that absorb at different wavelengths emitted from the respective light sources.

19. The method of claim 1, further comprising determining several contaminants that absorb at different wavelengths emitted from the respective light sources.

* * * * *

UNITED STATES PATENT AND TRADEMARK OFFICE
CERTIFICATE OF CORRECTION

PATENT NO. : 8,289,517 B2
APPLICATION NO. : 12/593172
DATED : October 16, 2012
INVENTOR(S) : A. Miklos et al.

It is certified that error appears in the above-identified patent and that said Letters Patent is hereby corrected as shown below:

In Column 9, Line 29 (Claim 7, Line 1), "final" should read --signal--.

Signed and Sealed this
Fifth Day of February, 2013

Teresa Stanek Rea
*Acting Director of the United States Patent and Trademark Office*